(12) United States Patent
Cowing

(10) Patent No.: US 6,210,672 B1
(45) Date of Patent: Apr. 3, 2001

(54) TOPICAL IMMUNOSTIMULATION TO INDUCE LANGERHANS CELL MIGRATION

(75) Inventor: Carol Cowing, San Diego, CA (US)

(73) Assignee: Torrey Pines Institute for Molecular Studies, San Diego, CA (US)

( * ) Notice: Subject to any disclaimer, the term of this patent is extended or adjusted under 35 U.S.C. 154(b) by 0 days.

(21) Appl. No.: 09/176,044

(22) Filed: Oct. 20, 1998

(51) Int. Cl.⁷ .................................................. A61K 39/00
(52) U.S. Cl. ..................................... 424/184.1; 424/277.1
(58) Field of Search ............................... 424/184.1, 277.1

(56) References Cited

U.S. PATENT DOCUMENTS

| | | | |
|---|---|---|---|
| 4,683,200 | 7/1987 | Hirohashi et al. | 435/68 |
| 4,861,589 | 8/1989 | Ju | 424/93 |
| 5,202,130 | 4/1993 | Grant et al. | 424/617 |
| 5,316,920 | 5/1994 | Tedder et al. | 435/69.3 |
| 5,980,898 | 11/1999 | Glenn et al. | |

OTHER PUBLICATIONS

Yechiel Becker, Dengue Fever Virus and Japanese Encephalitis Virus . . . , Virus Genes 9:1, pp. 33–45 (1994).

Yechiel Becker, An Analysis of the Role of Skin Langerhans Cells (LC in the Cytoplasmic Processing of HIV–1 Peptides . . . , Virus Genes 9:2, pp. 133–147 (1994).

James W. Young, et al., Dendritic Cells as Adjuvants for Class I Major Histocompatibility Complex–Restricted Antitumor Immunity, J. Exp. Med. vol. 183, pp. 7–11 (1996).

Laurence Zitvogel, et al., Therapy of Murine Tumors with Tumor Peptide–pulsed Dendritic Cells, J. Exp. Med., vol. 183, pp. 87–97 (1996).

Christina Celluzzi, et al., Peptide–Pulsed Dendritic Cells Induce Antigen–specific CTL–Mediated Protective Tumor Immunity, J. Exp. Med., vol. 183, pp. 283–287 (1996).

Paola Paglia, et al., Murine Dendritic Cells Loaded In Vitro with Soluble Protein . . . , J. Exp. Med., vol. 183, pp. 317–322 (1996).

Samir Mitragotri, et al., Ultra–sound Mediated Transdermal Protein Delivery, Science, vol 269, pp. 850–853 (Aug. 1995).

Jacques Banchereau, et al., Dendritic Cells and the Control of Immunity, Nature, vol. 293, pp. 245–252 (Mar. 1998).

Kenjiro Matsuno, et al., A Life Stage of Particle–laden Rat Dendritic Cells In Vivo . . . , J. Exp. Med., vol. 183 pp. 1865–1878 (Apr. 1996).

M. C. Udey, Cadherins and Landerhans Cell Immunobiology, Clin Exp. Immunol, vol. 107 (Suppl. 1), pp. 6–8 (1997).

A. Larregina, et al., Flow Cytometric Analysis of Cytokine Receptors on Human Langerhans Cells, Immunology, vol. 87, pp. 317–325 (1996).

B. Wang, et al., Tumour Necrosis Factor Reception II . . . , Immunology, vol. 88 pp. 284–288 (1996).

Aimin Tang, et al., Suppression of Murine Allergic Contact Dermatitis . . . , The Journal of Immunology, vol. 157, pp. 117–125 (1996).

Vanbever, et al., "Transdermal Delivery of Metroprolol by Electroporation", Pharmaceutical Research, vol. 22, No. 22, 1994.

*Primary Examiner*—Sheela Huff
(74) *Attorney, Agent, or Firm*—Knobbe, Martens, Olson & Bear, LLP

(57) ABSTRACT

Disclosed is a method for enhancing an immune response against an antigen by topical administration of an antigen or a portion thereof in conjunction with an enhancer of skin penetration and an inducer of Langerhans cell migration.

21 Claims, 7 Drawing Sheets

SEQUENCE LISTING

<160> NUMBER OF SEQ ID NOS: 1

<210> SEQ ID NO 1
<211> LENGTH: 8
<212> TYPE: PRT
<213> ORGANISM: Chicken ovalbumin

<400> SEQUENCE: 1

Ser Ile Ile Asn Phe Glu Lys Leu
1               5

US 6,210,672 B1

TOPICAL IMMUNOSTIMULATION TO INDUCE LANGERHANS CELL MIGRATION

Research related to this invention was supported in part by a grant, RO1 AI34168, from the National Institutes of Health to Carol O. Cowing.

BACKGROUND OF THE INVENTION

The body's first line of defense against pathogens is the skin. The outermost layer, the stratum corneum, is a broad zone of 20 to 30 cell layers thick. The dead cell remnants which comprise the stratum corneum are almost completely filled with keratin fibrils and surrounded by highly ordered lipid bilayers. As long as the epidermis is unbroken, the heavily keratinized stratum corneum presents a formidable physical barrier to entry for most foreign substances. The mucous membranes which line the digestive, respiratory, urinary and reproductive tracts, provide a similar, but less formidable physical barrier, lacking the thick stratum corneum.

The epithelium of both skin and mucous membranes is richly populated with immature dendritic cells, called Langerhans cells. These phagocytic leukocytes are poised for capture of antigens which may enter the epidermis through physical breaches in the stratum corneum. After physical trauma to the skin, signals are generated that induce Langerhans cells to leave the epidermis and migrate into the dermis and through afferent lymphatics to lymph nodes, carrying with them any antigens which had penetrated the protective stratum corneum (i.e. viral, bacterial, parasitic, allergic). Very small, lipophilic molecules, and some highly reactive molecules known as skin sensitizing agents, such as TNCB, poison ivy catechol, oxazolone, etc., may penetrate the intact stratum corneum, subsequently binding to proteins in the underlying epidermis and activating Langerhans cells.

Captured protein antigens are internalized and degraded by the Langerhans cells to yield small peptides which are incorporated into the peptide binding grooves of MHC molecules. The MHC-peptide complexes are then inserted into the plasma membranes for presentation to T cell receptors. During their migration to the lymph nodes, the Langerhans cells differentiate into mature dendritic cells, losing their phagocytic properties and instead, expressing high levels of MHC class I and II molecules as well as costimulatory and adhesion molecules, essential for effective antigen presentation (Udey, Clin. Exp. Immunol. 107:6–8, 1997). While it is now well known that Langerhans cells migrate from the epithelium to the T cell areas of the draining lymph nodes, relatively little is known about the signals which induce migration and differentiation of the Langerhans cells. In any event, once in the lymph nodes, the differentiated Langerhans cells bearing MHC-peptide complexes activate primary CD4+ helper T cells and CD8+ cytolytic T cells. These newly differentiated Langerhans cells which are recent immigrants to the lymph nodes are the most potent inducers of T cell immunity known.

It has recently been demonstrated that mouse or human dendritic cells exposed to tumor antigens or peptides are effective inducers of tumor-specific immunity that can eliminate or suppress even established tumors (Young and Inaba, J Exp. Med. 183:7–11, 1996; Zitvogel et al., J. Exp. Med 183:87–97, 1996; Celluzzi et al., J. Exp. Med 183:283–287, 1996; and Paglia et al., J. Exp. Med 183:317–322, 1996; incorporated herein by reference). In these studies, dendritic cells from bone marrow or blood were harvested, expanded in tissue culture, exposed to tumor antigens in vitro, and finally re-injected into the donor. Such individualized therapy is necessary in an outbred population to ensure that the appropriate, syngeneic MHC molecules are used for an individual's T cells and target tumor cells. While highly effective, this individualized procedure is too cumbersome, time consuming and costly to be a broadly applicable therapeutic measure.

SUMMARY OF THE INVENTION

A topical vaccination procedure is disclosed for enhancing an immune response against an antigen. Antigens from tumors, viral and bacterial pathogens, as well as parasites are encompassed within the scope of the present invention. The method involves administering the antigen in conjunction with: 1) a means for enhancing penetration of the antigen through the skin or mucous membranes, and 2) an agent for inducing Langerhans cell migration to the lymph nodes. The antigen is preferably a peptide of 3–20 amino acid residues in length, but can be any length that the Langerhans cell can process or insert into an MHC binding groove and which a T cell can recognize. The antigen is preferably administered at a concentration range of about 1 μg/ml to about 100 mg/ml.

Means for enhancing penetration of the antigen include, use of a lipophilic vehicle or penetration enhancer, such as dimethylsulfoxide (DMSO) or azone, low frequency ultrasound, electroporation, iontophoresis, intraepidermal delivery, and combinations thereof. Preferably, peptide penetration of the stratum corneum is facilitated by dimethylsulfoxide in combination with one of the physical transdermal delivery means.

Agents which induce Langerhans cell migration are selected from the group consisting of dibutylphthalate, dibutyl-D-tartarate, N,N-diethyl-toluamide, dibutylfumarate, di(2-ethylhexyl)fumarate, diisooctylmaleate, diethylhexylmaleate, diisooctylfumarate, benzoic acid, benzalkoniumchloride, camphor, bihenylmaleate, dioctylphthalate, dibutylmaleate, dioctymaleate, dibutylsuccinate, dioctylsuccinate, dinonylphthalate, diisononylphthalate, dimethylphthalate, diethylphthalate, dipropylphthalate, diphenylphthalate, dibenzylbutylphthalate, and diethylmethylphthalate. Low frequency ultrasound may also be employed as an inducer of Langerhans cell migration. Preferably, dibutylphthalate is administered to induce Langerhans cell migration.

DETAILED DESCRIPTION OF THE INVENTION

According to the present invention, an antigen is administered topically for uptake by an individual's own Langerhans cells. A lipophilic solvent is preferably included to facilitate penetration of the antigen through the stratum corneum and into the underlying epidermis. In one embodiment of the present invention, a physical stimulus, such as low frequency ultrasound or an electric field, may be applied to the skin following the topical administration, in order to enhance antigen penetration through the stratum corneum. The administration of antigen to the skin is accompanied by the topical application of further agent(s), such as dibutylphthalate, which induce Langerhans cell migration to the draining lymph node.

Induction of Langerhans Cell Migration by Dibutylphthalate

Figure 1:
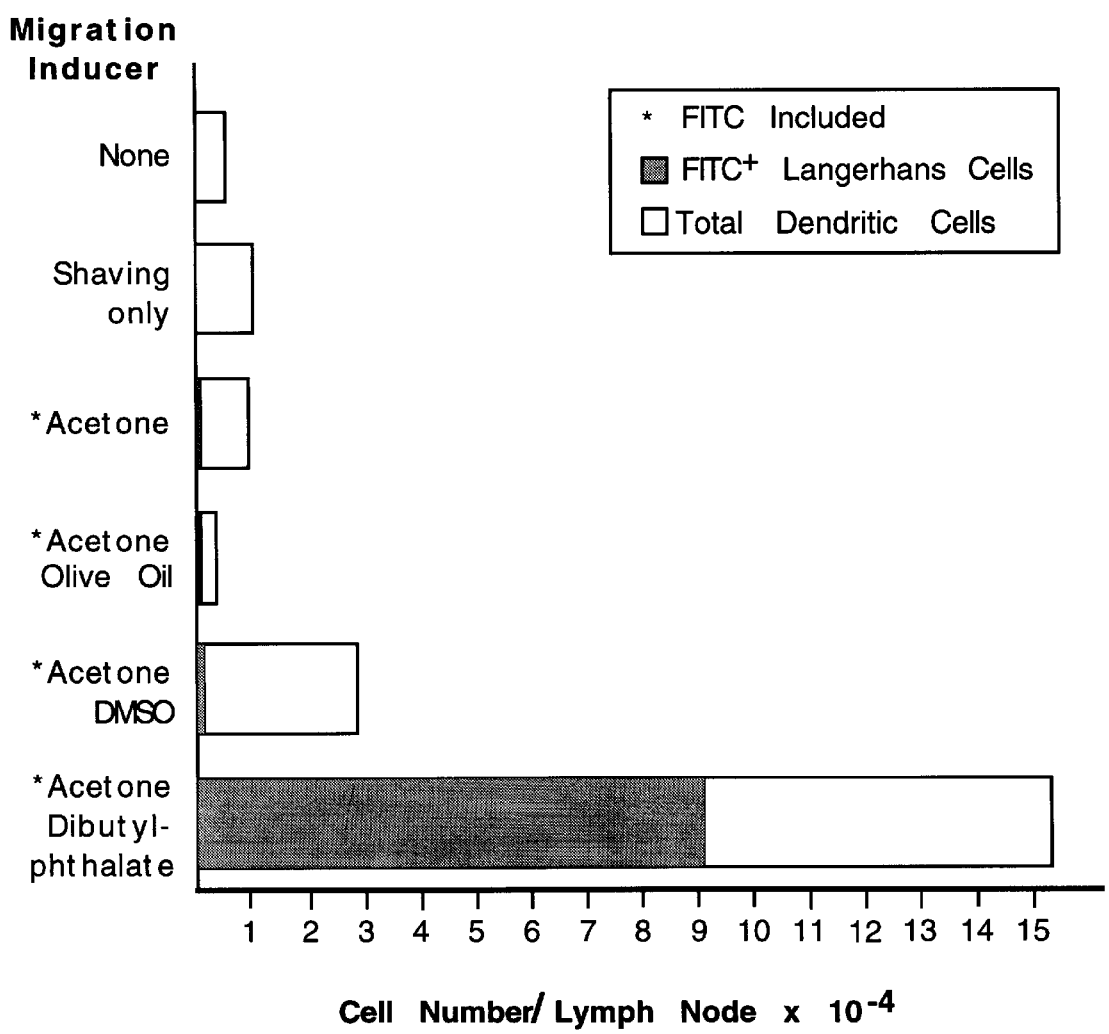
FIG. 1 illustrates the effect of the various treatment regimens on total and FITC+ lymphoid dendritic cells 2 days after treatment.

Fluorescein isothiocyanate (FITC) has been used extensively by the inventor and others, to characterize Langerhans cell migration. FITC is a small (mw 389) non-peptide, largely lipophilic molecule, capable of crossing the stratum corneum. Immunogenicity of FITC is due to the reactivity of its isothiocyanate group (—N=C=S) with free amino groups, permitting it to be covalently bound to proteins and/or peptides. C57BL/6 mice received the following treatments: 1) none; 2) abdomen shaving only; 3) topical administration of FITC in acetone; 4) topical administration of FITC in acetone and olive oil; 5) topical administration of FITC in acetone and DMSO diluted in phosphate buffered saline (PBS); and 6) topical administration of FITC in acetone and dibutylphthalate. The draining inguinal lymph nodes were then examined for immigrant Langerhans cells by immunofluorescent flow cytometry each day thereafter. Migratory Langerhans cells were identified by the presence of FITC and expression of high MHC class II molecules or by a Langerhans cell-specific monoclonal antibody (NLDC-145). Other dendritic cell residents of the lymph nodes could also be differentiated using a dendritic cell-specific monoclonal antibody, 33D1. The uptake of FITC and the Langerhans cell response to migratory signals were observable in the draining lymph node as early as six hours after topical administration. However, 48–72 hours was required for maximal immigration of Langerhans cells into the lymph node. FIG. 1 illustrates the effect of the various treatment regimens on total and FITC+ lymphoid dendritic cells 2 days after treatment. In animals administered FITC in acetone, there was no enhancement in FITC+ Langerhans cell number induced by olive oil or dimethylsulfoxide (DMSO), although DMSO had a modest stimulatory effect on non-specific immigration, suggesting that antigen contact and Langerhans cell migration are independently regulated. The addition of dibutylphthalate had a striking effect on both FITC+ and total dendritic cell migration into the lymph node. Thus, dibutylphthalate was a very potent migration inducer.

Figure 2:
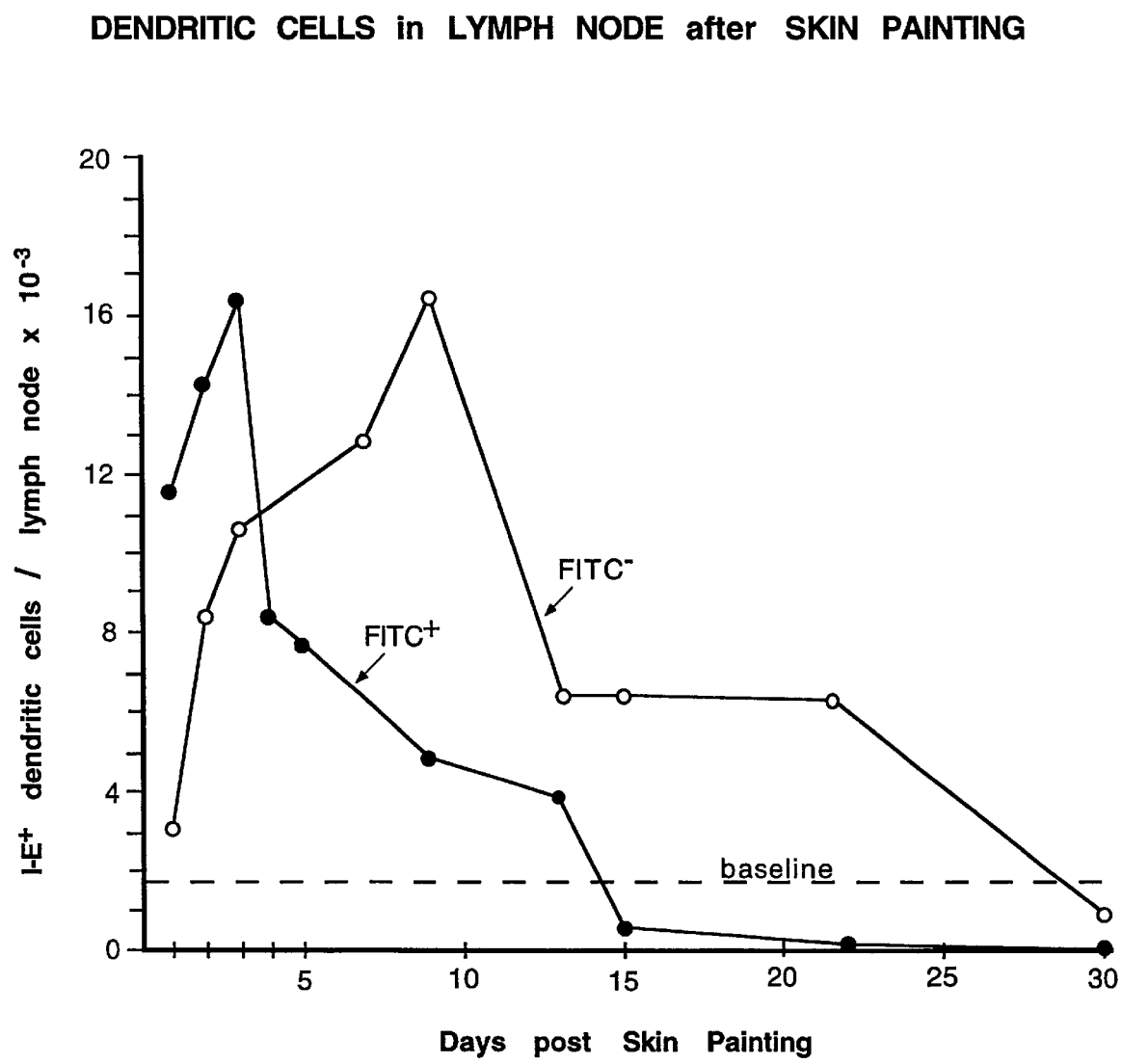
FIG. 2 shows the kinetics of Langerhans cell migration in response to FITC in acetone and dibutylphthalate.
Figure 3:
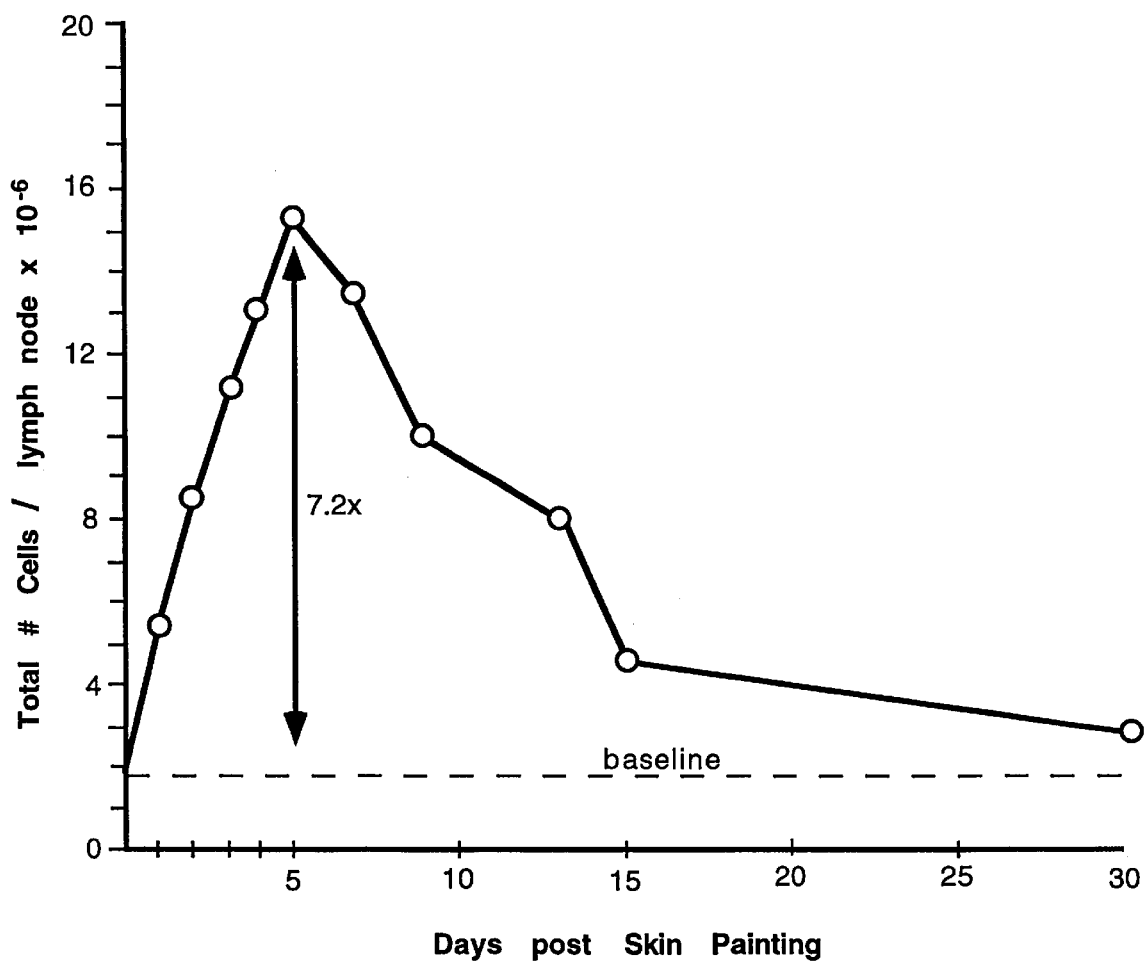
FIG. 3 shows the effect of topical administration of FITC in acetone and dibutylphthalate on total lymph node cell number.

In mice treated with FITC in acetone and dibutylphthalate, the kinetics of Langerhans cell migration is shown in FIG. 2. High numbers of FITC+ Langerhans cells were present in the lymph node by 12 hours and the peak frequency of immigrant FITC+ Langerhans cells occurred about 2 to 3 days following topical administration. Note however, that in addition to inducing the migration of FITC+ Langerhans cells, the number of unlabeled dendritc cells was also markedly enhanced, reaching peak levels 9–10 days following treatment. The unlabeled dendritic cells could be Langerhans cells that had lost the FITC label. Total lymph node cells in response to the topical administration is shown in FIG. 3. Five days after skin painting, the lymph node cell population had increased by approximately 7.2 fold over baseline levels. These results indicate that antigen (FITC) in acetone and dibutylphthalate not only stimulated antigen+ Langerhans cell migration, but also resulted in a dramatic T and B cell response in the draining lymph node.

Induction of Langerhans Cell-Mediated Tumor-Specific Immunity

The C57BL/6 thymoma tumor cell line, EL4, was transfected with the complete gene for chicken ovalbumin (OVA). The resulting transfected cell line, EG7-OVA, expresses chicken ovalbumin. An eight amino acid peptide, OVA 257-264, with the sequence, SIINFEKL (SEQ ID NO: 1), is expressed in the MHC class I molecule $K^b$, where it has been demonstrated to function as a tumor-associated peptide antigen for CD8+ CTLs both in vivo and in vitro (Celluzzi et al., *J. Exp. Med* 183:283 (1996)). Based on the positive results using FITC, the inventors followed a similar protocol in an attempt to induce immunity to the EG7-OVA tumor by topical administration of the well-characterized, synthetic SIINFEKL (SEQ ID NO: 1) tumor-associated peptide.

Figure 4:
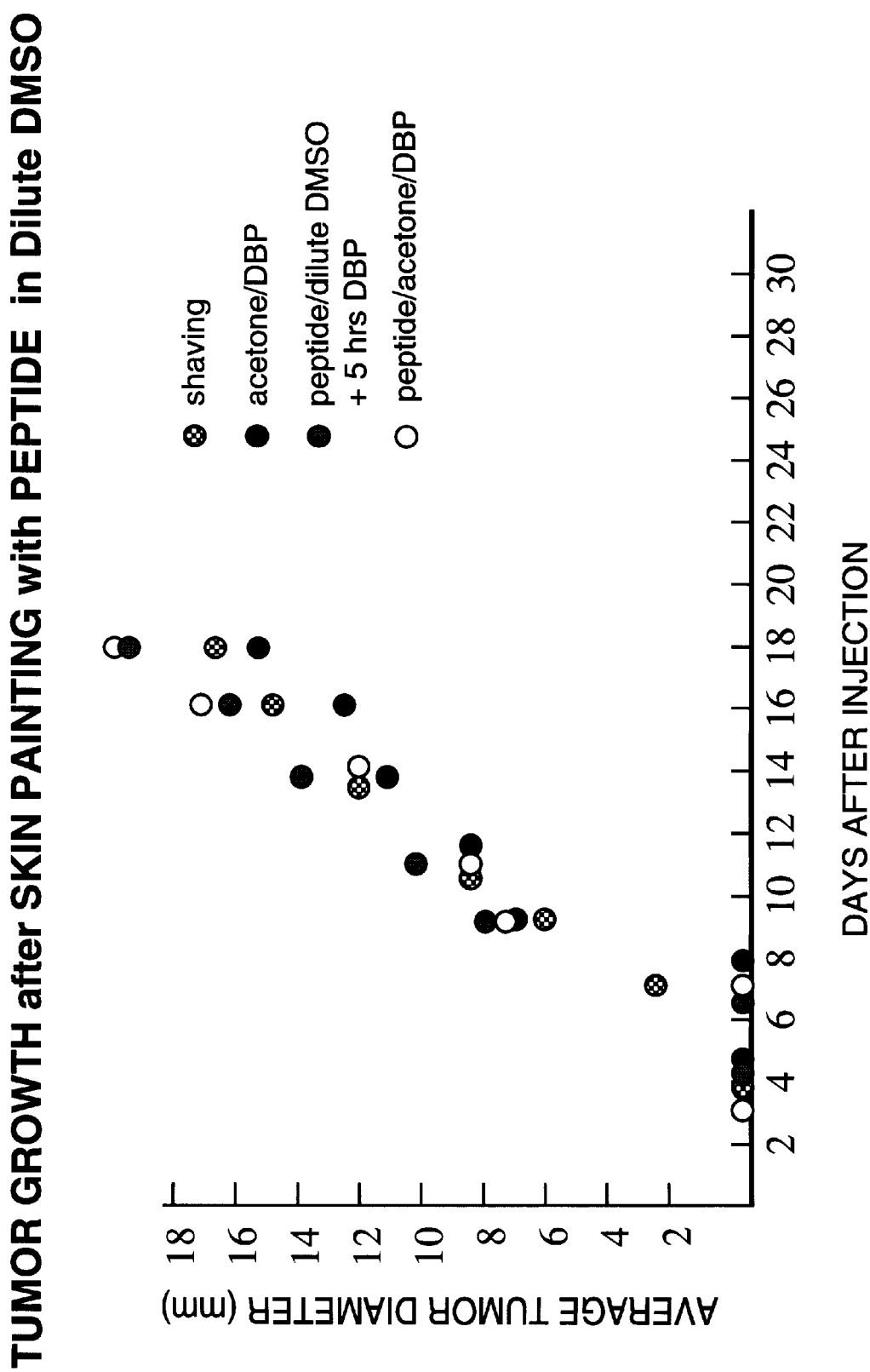
FIG. 4 shows poor inhibition of EG7-OVA tumor growth by cutaneous topical administration of the tumor peptide SIINFEKL (SEQ ID NO.1) in acetone and dibutylphthalate.

C57BL/6 mice were treated as follows: 1) shaving alone; 2) topical administration of acetone and dibutylphthalate; 3) SIINFEKL (SEQ ID NO: 1) (240 μg/ml) in DMSO diluted in PBS, followed in 5 hours by acetone and dibutylphthalate; and 4) SIINFEKL (SEQ ID NO: 1) (240 μg/ml) in acetone and dibutylphthalate. All mice were subsequently injected subcutaneously with $5 \times 10^5$ EG7-OVA cells (5-times the minimal tumorogenic dose). Tumor-specific immunity was monitored by measuring tumor size. The results shown in FIG. 4, indicate that none of the treatment protocols were effective in inhibiting tumor cell growth. Since it was known from the FITC experiments that dibutylphthalate was a potent Langerhans cell migration inducer, and that SIINFEKL (SEQ ID NO: 1) was readily incorporated into the MHC class I molecule $K^b$ where it activated CD8+ CTLs (Celluzzi et al., *J. Exp. Med* 183:283 (1996)), it was concluded that the SIINFEKL peptide did not get across the stratum corneum.

Figure 5:
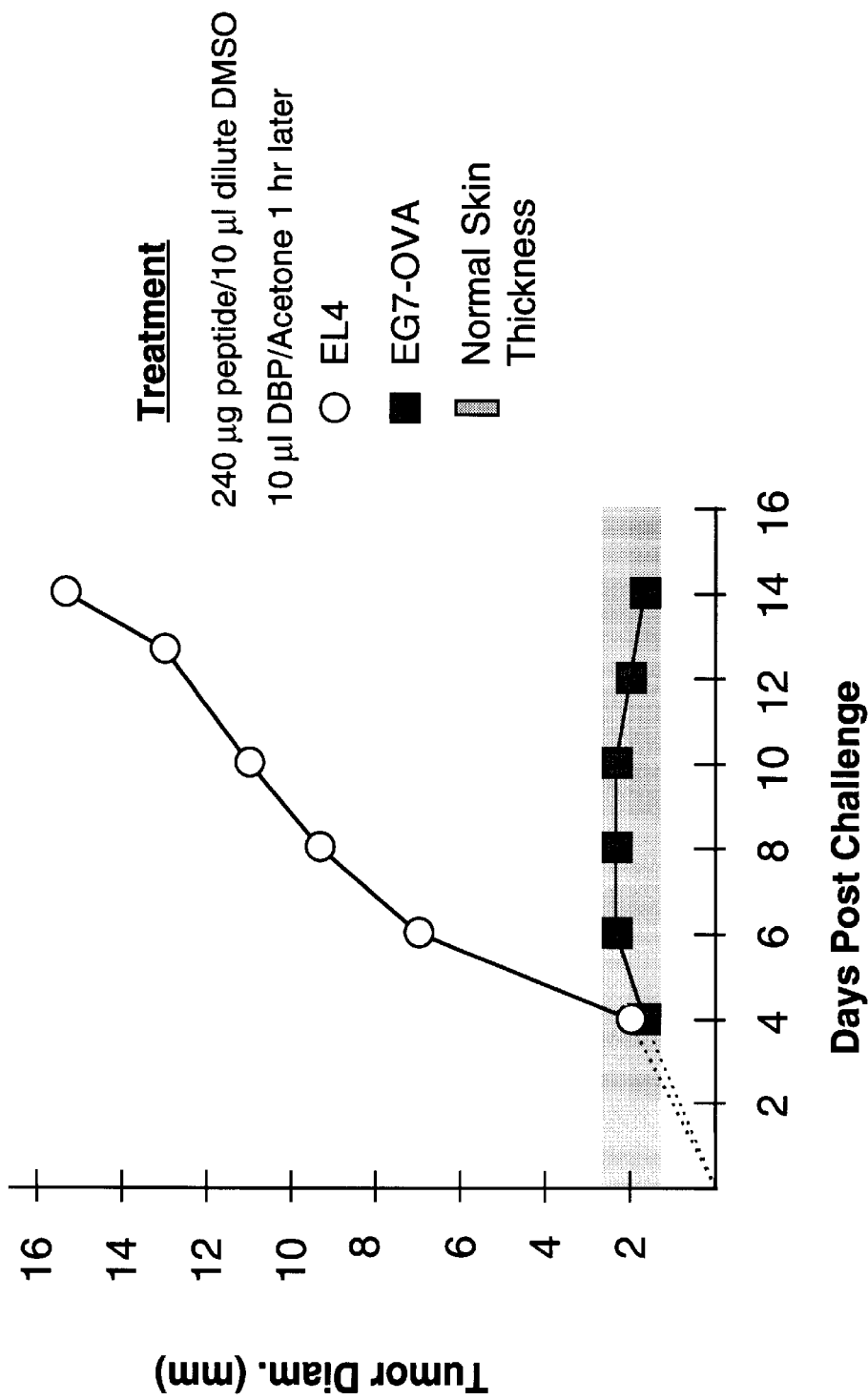
FIG. 5 illustrates the induction of complete EG7-OVA tumor-specific immunity by intravaginal topical application of SIINFEKL (SEQ ID NO.1) in acetone and dibutylphthalate.

Since it was postulated that topical administration of SIINFEKL (SEQ ID NO: 1) in acetone and dibutylphthalate had failed to confer tumor-specific immunity because the peptide did not penetrate the stratum corneum, the same topical vaccine was applied intravaginally. The mucous membranes lack the tough barrier posed by the stratum corneum. The results shown in FIG. 5 suggested that complete protection against the tumor was induced by SIINFEKL (SEQ ID NO: 1) in acetone and dibutylphthalate. The EL4 parent tumor cell line, lacking chicken ovalbumin, was used as a positive control; no immunity against the EL4 tumor cells was seen. Thus, the inventors' hypothesis regarding penetration of the stratum corneum was confirmed; the SIINFEKL (SEQ ID NO: 1) peptide was not reaching the Langerhans cells underlying the stratum corneum.

Figure 6:
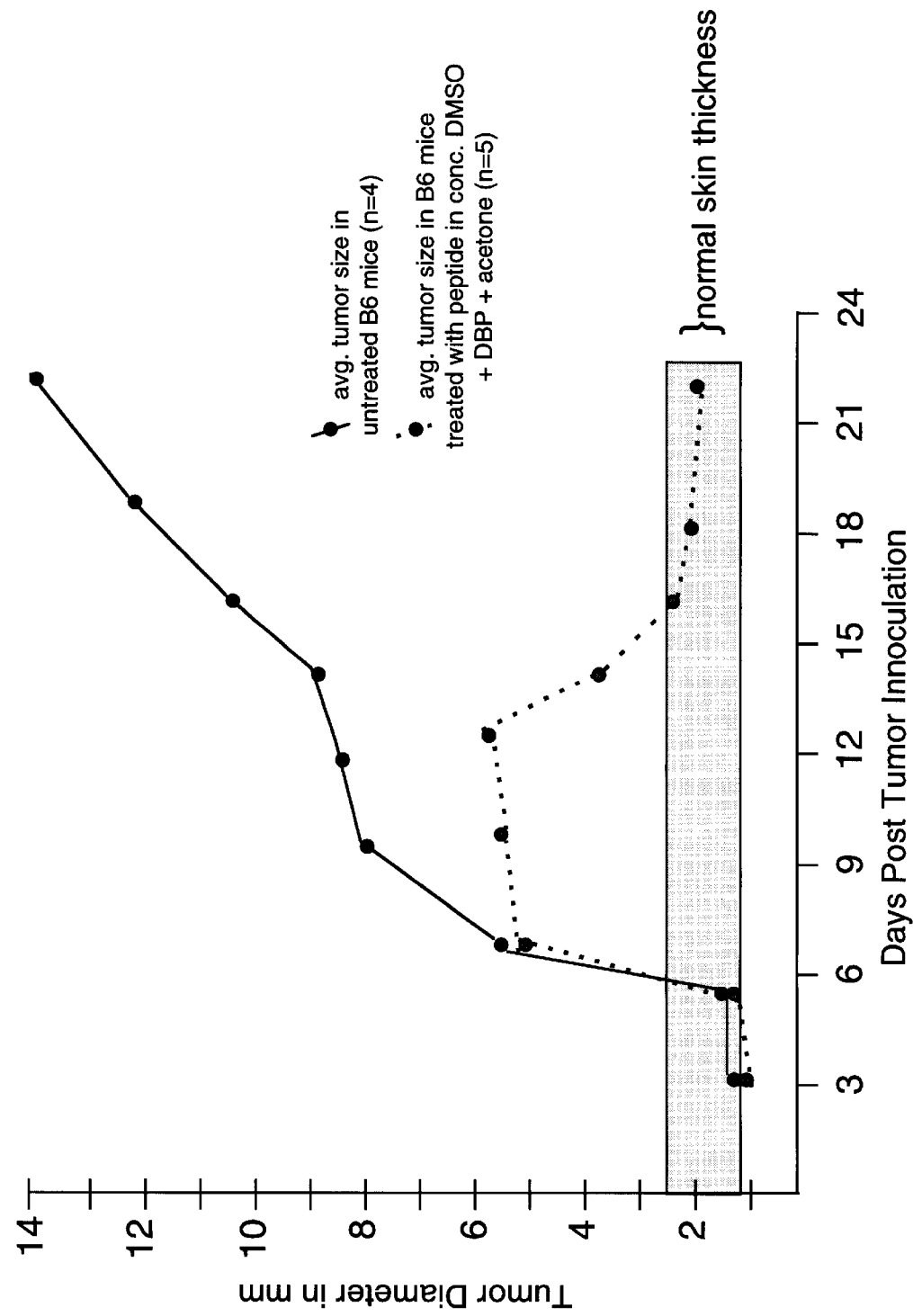
FIG. 6 shows complete inhibition of EG7-OVA tumor growth by cutaneous topical administration of SIINFEKL (SEQ ID NO.1) in concentrated DMSO, followed by dibutylphthalate in acetone.

While intravaginal topical administration of tumor antigen provided an effective means of routing antigen to the Langerhans cells for subsequent induction of tumor-specific immunity, mucous membrane application sites, like the vagina, are not well- suited for convenient use and monitoring by general practitioners likely to be involved in administering the topical vaccinations of the present invention. Thus, to enhance the effectiveness of cutaneous topical administration, SIINFEKL (SEQ ID NO: 1) was dissolved in DMSO and applied to the skin without dilution. Dibutylphthalate in acetone was applied to the same site 5 hr later. All mice were subsequently injected subcutaneously with 5×10[5] EG7-OVA cells. The results shown in FIG. 6 indicate that the peptide in DMSO was able to traverse the stratum corneum, effectively gaining access to the Langerhans cells. Tumor growth was suppressed after 6 to 9 days and even the established tumors were completely eliminated by 16 days post-inoculation. Thus, the tumor-specific peptide, SIIN-FEKL (SEQ ID NO: 1), in concentrated DMSO, penetrated the stratum corneum, was incorporated into the MHC class I molecule $K^b$ on epidermal Langerhans cells, and in the presence of the migration inducer, dibutylphthalate, was effectively presented to CD8+ CTLs in the lymph nodes.

Antigen Source

"Antigen" as used herein, includes any molecule which when administered in accordance with the present invention is capable of eliciting antigen-specific immunity. Accordingly, the antigen or a fragment thereof must be able to (1) penetrate the skin or mucous membrane, (2) interact with Langerhans cells in the epidermis or epithelium of mucous membranes, (3) associate in whole or in part with an MHC class I or II molecule on a Langerhans cell, and (4) activate T cell receptors on CD4+ or CD8+ T cells, conferring antigen-specific immunity. More particularly, the topical vaccination method of the present invention is directed toward antigens from tumor cells, viral and bacterial pathogens and parasites.

Small peptide antigens are particularly preferred, although not essential, as it is easier to get smaller peptides (about 3–20 amino acid residues) across the stratum corneum and into the epidermis than larger proteins. Furthermore, properly sized peptides, like SIINFEKL (SEQ ID NO: 1), are more likely to bind directly to MHC molecules on the Langerhans cell surface through the process of peptide exchange, in which the exogenously added peptides displace those endogenous peptides, which may exhibit a lower affinity for the peptide binding groove of the MHC class I or II molecules. Characteristics of peptides suitable for direct association with class I or II MHC molecules have been studied extensively. Thus, those skilled in the art would be able to predict, based upon peptide structure, sequences likely to associate with a given MHC. Peptides which bind effectively to class I MHC molecules are generally comprised of about 8–9 amino acid residues, whereas peptides which associate preferentially with the class II MHC molecules are about 11–14 amino acid residues in length. Indeed, some antigenic peptides capable of interacting directly with MHC molecules on dendritic cells are known and can be synthesized by standard techniques.

Alternatively, while specific tumor-associated antigens have been identified for many human tumors, the relevant peptides are often unknown. Nonetheless, crude acid-eluted tumor peptides can be prepared quickly and easily and have been shown to be effective inducers of tumor-specific immunity when associated with dendritic cells (Zitvogel et al., *J. Exp. Med* 183:87–97, 1996). Thus, both known, homogeneous preparations of synthetic peptides, as well as unknown mixtures of extracted peptides, may be suitable for use in the present invention. The choice and preparation of suitable peptide antigens is well within the skill of those in the art. See below for a detailed description of specific working examples.

Non-peptide immunogenic compounds capable of induction of specific immunity are also contemplated as potential antigens in accordance with the present invention. Small non-peptide haptens may covalently bind to peptides or proteins after crossing the stratum corneum, thereby gaining access to standard antigen presentation pathways, through association with an MHC molecule. For example, the immunogenicity of FITC was shown to be due to the reactivity of its isothiocyanate group (—N=C=S) with free amino groups, permitting it to be covalently incorporated within proteins and/or peptides. Thus, non-peptide antigenic moieties, from tumor cells, pathogens, parasites, allergens, etc., may be used in practicing the topical vaccination methods of the present invention.

It should be noted that choice of the source of antigen is not critical to the invention, which is a general method for enhancing antigen-specific immunity. However, the specific immune response obtained will, of course, depend on the particular antigen employed. It is the manner of topical administration, the penetration of the stratum corneum, the induction of Langerhans cell migration and the subsequent antigen presentation by MHC and MHC-like-dependent pathways, which individually or in combination, exemplify the features of the disclosed invention. The fact that no limitations are placed on the selection of antigens from a wide variety of sources is consistent with use of the basic methods for inducing antigen-specific immunity against many antigens. Thus, the choice of a particular antigen and its source will depend on the application and is within the ordinary skill of those in the field of immunology.

Penetration of the Stratum Corneum

The outer layer of the skin is designed to resist entry of foreign materials into the body. Because it is formed of densely packed layers of keratinocyte cell membranes and keratin fibrils, the stratum corneum is impermeable to most molecules of higher molecular mass, particularly those of a hydrophilic nature. Consequently, only a few drugs are administered transdermally. Such molecules are typically small and lipophilic. The transdermal delivery of peptides is ill-favored because of their hydrophilicity and generally high molecular mass. Numerous studies document the great difficulty in getting peptides through the stratum corneum (For review, see Steinstrasser and Merkle, *Pharm. Acta. Helv.* 70:3–24 (1995)). Among the approaches which have yielded some success in enhancing peptide penetration are included lipophilic vehicles, low frequency ultrasound, electroporation, iontophoresis, and intraepidermal delivery. These are considered below.

Lipophilic Solvents

Lipophilic solvents like acetone, azone, and dimethylsulfoxide (DMSO) are known to penetrate the stratum corneum. As discussed above, the inventor has found that small peptides, like SIINFEKL, dissolved in DMSO cross the stratum corneum and enter the lower strata of the epidermis. Thus, the present disclosure with respect to antigen penetration enhancers, encompasses a variety of lipophilic solvents, including DMSO, and symmetrical or unsymmetrical sulfide and sulfoxides where the alkyl group contains 1 to 16 carbon atoms, as well as liposomes.

Where lipophilic penetrants, such as DMSO, are employed in the present invention to enhance peptide penetration, such solvents may be administered neat or diluted with other solutions, such as PBS. Ratios of mixtures may range from about 1:9 to about 9:1 (penetrant to diluant). Preferably, the penetration enhancer is undiluted.

Low Frequency Ultrasound

Mitragotri et al. reported that even large protein molecules, such as insulin (mw 6,000), IFN-γ (mw 17,000), and erythropoietin (mw 48,000) could be coaxed into crossing the stratum corneum, at about 12% efficiency, using low frequency ultrasound (Mitragotri et al., *Science* 269:850–853 (1995); incorporated herein by reference).

Ultrasound works on skin by non-thermal, cavitational effects, creating micro-bubbles that expand and contract in the stratum corneum, resulting in a transient increase in permeability. Cavitation occurs at much lower frequency sound waves (i.e. about 20 kHz) than traditional diagnostic imaging (2–12 Mhz); both applications requiring an intensity of approximately 0.2 W/cm.

Electroporation

Vanbever et al. disclosed that about 10% of the small (mw 267) molecule, metoprolol, could be transported across the skin during 4 hr after 5 single 450 V pulses (Vanbever et al., *Pharm. Res.* 11:1000–1003 (1994); incorporated herein by reference). Electroporation has been used extensively for permeabilization of cell membranes for the purpose of getting DNA into cells. Transdermal transport of peptides may be accomplished by localized exposure of the skin to high intensity electric field pulses, which may create transient aqueous pores in the lipid bilayers.

Iontophoresis

Bodde et al. found that only about 0.4% per hour of vassopressin (mw 1084) crossed the stratum corneum (Bodde et al., *Biochem. Soc. Trans.* 17:943–945 (1990); incorporated herein by reference). Iontophoresis involves exposing the skin to low intensity current. Polar molecules move in response to the current. However, transport is believed to occur via glands or hair follicles which project through the epidermis down into the dermis. Consequently, the method may not be ideally suited for providing access of the epidermal Langerhans cells to the permeating peptides. Nonetheless, the method is encompassed within the present invention.

Intraepidermal Delivery

Certainly, the stratum corneum can be penetrated using sharp instruments. Thus, intraepidermal injections using traditional beveled needles and syringes is possible. Similarly, introduction of the antigenic agents into the epidermis using pronged instruments, like those used for administration of the tine test, is also possible. Such invasive physical methods may solve the penetration problem and may even provide concomitant migratory signals to the Langerhans cells. However, such methods may also defeat some of the key advantages of the present invention, such as the ease of topical application without the need for sterile instruments or highly skilled health care personnel. Furthermore, the use of invasive procedures are always accompanied by increased risks of infection.

Induction of Langerhans Cell Migration

While effectively bringing antigens into contact with the Langerhans cells in the epidermis is necessary for practice of the present topical vaccination method, it is not by itself sufficient to induce the strong antigen-specific immunity desired for a vaccination procedure. Indeed, it is the second step, the induction of Langerhans cell migration, which remained obscure for so long until the present disclosure. Although the phenomenon of Langerhans cell migration from the epithelium to the lymph nodes has been well known for many years, the complex regulatory pathways which control Langerhans cell migration and differentiation in vivo are not well understood. Moreover, there are apparently a number of commonly held misconceptions regarding Langerhans cell migration. For example, some investigators believe that the spontaneous and/or continuous migration of Langerhans cells is sufficient for induction of antigen-specific immunity (see e.g. Matsuno et al., *J. Exp. Med* 183:1865 (1996)). Others in the field believe that contact sensitizing antigens are capable of inducing Langerhans cell migration by themselves, and therefore presume that a separate induction stimulus is not needed for any antigens (see e.g. Udey, *Clin. Exp. Immunol.* 107:6 (1997)). Accordingly, scientists using FITC in acetone and dibutylphthalate to study Langerhans cell migration believe that it is the antigen (FITC) which induces migration (see e.g. Wang et al., *Immunol.* 88:284 (1996)). In summary, the state of the art in this field today, contemplates neither the existence of exogenous inducers of Langerhans cell migration, nor a role for such inducers in enhanced antigen-specific immunity.

At present, inquiry into regulation of Langerhans cell migration focuses on the production of cytokines and chemokines by a variety of cells, which appear to modulate Langerhans cell migration and maturation in vitro. For instance, granulocyte-macrophage colony-stimulating factor (GM-CSF) and interleukin-1α (IL-1α) may mediate in vitro maturation (Larregina et al., *Immunology* 87:317–325, 1996). Tumor necrosis factor-α (TNF-α) is involved in Langerhans cell migration (Banchereau and Steinman, *Nature* 392:245 (1998)). Other factors implicated in the control of various aspects of Langerhans cell maturation and/or migration include MIP-1α, IL-4, G-protein-coupled receptors for the calcitonin-gene related peptide, C5a and other chemokines (Banchereau and Steinman, Nature 392:245 (1998)). Thus, while many possible signals and signaling pathways have been identified, the regulatory scheme remains obscure.

Furthermore, the elaborated signals and pathways discussed above tend to focus on the "normal" response to traumatic breaches in the epidermis. Exogenous inducers of Langerhans cell migration have not been considered before this work by the inventor. Indeed, researchers had not even recognized that stimulation of Langerhans cell migration was a critical step in the therapeutic induction of antigen-specific immunity.

In general, the types of compounds useful in the present invention are often diesters or diamides of an acid anhydride or dicarboxylic compound. The esters in this compound are typically formed of the dicarboxylic compound esterified with two groups selected independently from a 1 to 16 carbon alkyl moiety and/or aryl moiety. The aryl moieties are preferably substituted or unsubstituted benzyl or phenyl moieties. In one embodiment, both ester moieties are identical. In another embodiment, the ester moieties are different.

More particularly, compounds with the capacity to induce Langerhans cell migration may be represented by the general formula:

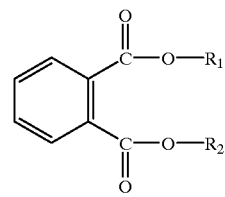

wherein $R_1$ and $R_2$ are independently, alkyl or aryl side chains containing from 1 to 16 carbon atoms. The aryl moieties are preferably substituted or unsubstituted benzyl or phenyl moieties. In one particularly preferred embodiment, the $R_1$ and $R_2$ groups are identical alkyl moieties from 2 to 6 carbons, such as dibutylphthalate, wherein $R_1$ and $R_2$ are $(CH_2)_3$—$CH_3$.

Other compounds which are potentially useful as inducers of Langerhans cell migration include those represented by the general formula:

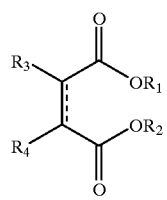

wherein $R_3$ and $R_4$ may be linked to form a cyclic ring and $R_1$ and $R_2$ are independently, alkyl and/or aryl side chains containing from 1 to 16 carbon atoms.

Compounds which are useful as inducers of Langerhans cell migration may be screened using the standard FITC methods described for the data presented in FIGS. 1–3. C57BL6 mice are shaved on their abdomens and painted with 100 μl test solution, containing 5 mg/ml FITC in a 50/50 (v/v) mixture of acetone and the migration inducer (e.g. dibutylphthalate). After 2 days, the draining inguinal lymph node is removed and the total number of dendritic cells (both FITC+ and FITC−) is determined by flow cytometry and MHC class II immunoassay.

Specific compounds encompassed within the present invention for induction of Langerhans cell migration are provided below:

| Abbreviation | Compound |
| --- | --- |
| DBP | dibutylphthalate |
| DBT | dibutyl-D-tartarate |
| DET | N,N-diethyl-toluamide |
| DBF | dibutylfumarate |
| DEHF | di(2-ethylhexyl)fumarate |
| DIOM | diisooctylmaleate |
| DEHM | di(ethylhexyl)maleate |
| DIOF | disooctylfumarate |
| BA | benzoic acid |
| BC | benzalkonium chloride |
| C | camphor |
| BM | bihenylmaleate |
| DOP | dioctylphthalate |
| DBM | dibutylmaleate |
| DOM | dioctylmaleate |
| DBS | dibutylsuccinate |
| DOS | dioctylsuccinate |
| DNP | dinonylphthalate |
| DINP | diisononylphthalate |
| DMP | dimethylphthalate |
| DEP | diethylphthalate |
| DPP | dipropylphthalate |
| DphP | diphenylphthalate |
| DBBP | dibenzylbutylphthalate |
| DMEP | diethylmethylphthalate |

Figure 7:
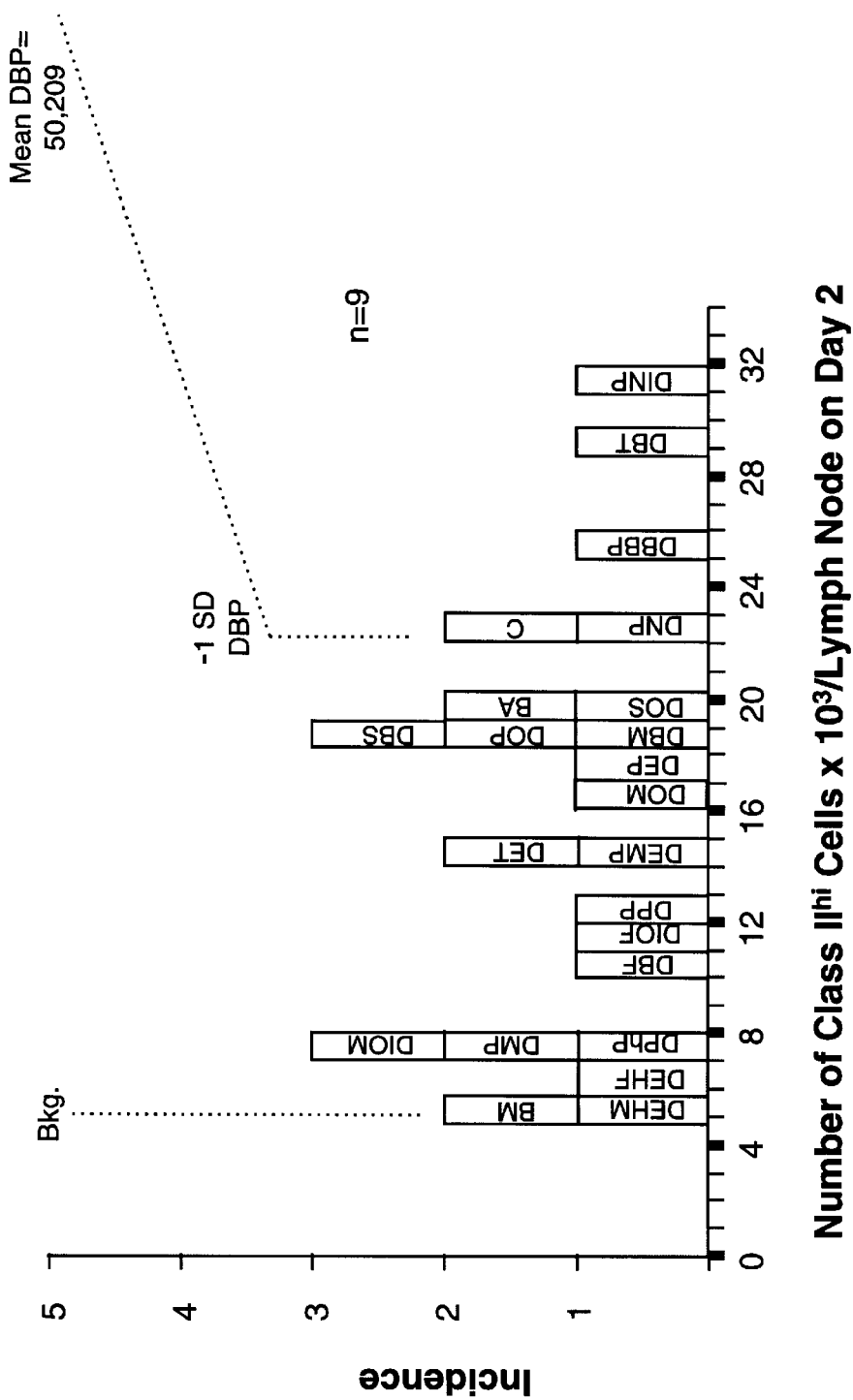
FIG. 7 shows the effect of various potential inducers of Langerhans cell migration in the FITC screening assay.

Test results are shown in FIG. 7. Total MHC class II$^{hi}$ cells were increased over background for most compounds tested. DNP, C, DBBP, DBT, and DINP were within 1 standard deviation of the positive control, dibutylphthalate (DBP).

Besides the chemical inducers of Langerhans cell migration, the inventor has found that low frequency ultrasound also exhibits positive results in the FITC migration screening procedure described above. Thus, in one embodiment of the present invention, low frequency ultrasound may be employed both as a penetrant and/or as an inducer of Langerhans cell migration.

The peptides/antigens used in accordance with the present invention may generally be applied topically to epidermal or epithelial sites in a dose range of approximately 1 μg/ml to about 100 mg/ml. Preferably, peptide antigens may be administered within the dose range of 1 mg/ml to 10 mg/ml. Topical administration to the skin may include from 0.01 to 1 ml/cm² application volumes, preferably about 0.05 to 0.5 ml/cm². Obviously, the larger the surface area that is treated the greater the number of Langerhans cells that will be induced to migrate to the draining lymph node. Routes of administration may be selected from any epidermal and/or mucous membrane sites including, the skin, intravaginal, rectal, aerosol delivery to the airways and lungs, and possibly administration to the GI tract for some antigens. Where chemical inducers of Langerhans cell migration are applicable, the chemical inducer may be given neat or mixed with an organic solvent, such as acetone, in a range of ratios from about 1:9 to about 9:1 (inducer to solvent), preferably in a range of ratios from about 3:7 to about 7:3, and most preferably at a ratio of approximately 1:1.

In some instances, it may be advantageous, merely to enhance Langerhans cell migration, without specifically administering any antigen. For example, where an individual has a skin cancer, such as melanoma or basal cell carcinoma, it may be useful in enhancing an immune response against the tumor to administer an inducer of Langerhans cell migration to sites surrounding the tumor, before surgery. Alternatively, topical administration may follow excision and subsequent chemotherapy and/or radiation.

While a number of preferred embodiments of the invention and variations thereof have been described in detail, other modifications and methods of use will be readily apparent to those of skill in the art. Accordingly, it should be understood that various applications, modifications and substitutions may be made of equivalents without departing from the spirit of the invention or the scope of the claims.

What is claimed is:

1. A topical method for enhancing an immune response against an antigen in a mammal comprising the steps of:
   administering to an epidermal or mucous membrane site on said mammal a composition comprising said antigen;
   administering to said epidermal or mucous membrane site a means for enhancing penetration of said antigen through the epidermis or mucous membrane, said means for enhancing penetration being selected from the group consisting of a lipophilic solvent, low frequency ultrasound, electroporation, iontophoresis and intraepidermal delivery; and
   administering to said epidermal or mucous membrane site a means for enhancing Langerhans cell migration.

2. The topical method of claim 1, wherein said antigen is a peptide of about 3–20 amino acid residues in length.

3. The topical method of claim 2, wherein said peptide is from 8–14 amino acids in length.

4. The topical method of claim 2, wherein said peptide is administered at a concentration in a range of about 1 μg/ml to about 100 mg/ml.

5. The topical method of claim 1, wherein said means for enhancing Langerhans cell migration comprises a compound of the formula:

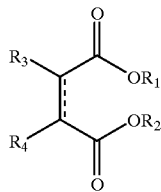

wherein $R_3$ and $R_4$ are linked to form a cyclic ring and $R_1$ and $R_2$ are independently, alkyl side chains containing from 1 to 16 carbon atoms.

6. The topical method of claim 5, wherein said means for enhancing Langerhans cell migration is selected from the group consisting of dibutylphthalate, dibutyl-D-tartarate, N,N-diethyl-toluamide, dibutylfumarate, di(2-ethylhexyl) fumarate, diisooctylmaleate, diethylhexylmaleate, diisooctylfumarate, benzoic acid, benzalkoniumchloride, bihenylmaleate, dioctylphthalate, dibutylmaleate, dioctymaleate, dibutylsuccinate, dioctylsuccinate, dinonylphthalate, diisononylphthalate, dimethylphthalate, diethylphthalate, dipropylphthalate, diphenylphthalate, dibenzylbutylphthalate, diethylmethylphthalate and camphor.

7. The topical method of claim 1, wherein said means for enhancing Langerhans cell migration is low frequency ultrasound.

8. The topical method of claim 6, wherein said means for enhancing Langerhans cell migration is dibutylphthalate.

9. The topical method of claim 1, wherein said means for enhancing Langerhans cell migration further comprises an organic solvent.

10. The topical method of claim 9, wherein said organic solvent is selected from the group consisting of symmetrical or unsymmetrical dialkyl ketones, where said alkyl group contains from 1 to 16 carbon atoms.

11. The topical method of claim 9, wherein said organic solvent is acetone.

12. A topical method for enhancing Langerhans cell migration in a mammal comprising the step of administering to an epidermal or mucous membrane site on said mammal, an effective amount of an inducer of Langerhans cell migration, said inducer being selected from the group consisting of low frequency ultrasound, dibutylphthalate, dibutyl-D-tartarate, N,N-diethyl-toluamide, dibutylfumarate, di(2-ethylhexyl)fumarate, diisooctylmaleate, diethylhexylmaleate, diisooctylfumarate, benzoic acid, benzalkoniumchloride, bihenylmaleate, dioctylphthalate, dibutylmaleate, dioctymaleate, dibutylsuccinate, dioctylsuccinate, dinonylphthalate, diisononylphthalate, dimethylphthalate, diethylphthalate, dipropylphthalate, diphenylphthalate, dibenzylbutylphthalate, diethylmethylphthalate and camphor.

13. The topical method of claim 1, wherein said lipophilic solvent is selected from the group consisting of a symmetrical alkylsulfide, an unsymmetrical alkylsulfide and an alkylsulfoxide, wherein said alkyl group contains from 1 to 16 carbon atoms.

14. The topical method of claim 13, wherein said alkylsulfoxide is dimethylsulfoxide.

15. The topical method of claim 1, wherein said antigen is from a source selected from the group consisting of tumors, viruses, bacteria and parasites.

16. A topical method for enhancing an immune response against an antigen in a mammal comprising the steps of:
   administering to an epidermal or mucous membrane site on said mammal a composition comprising said antigen;
   administering to said epidermal or mucous membrane site a dose of low frequency ultrasound sufficient to induce both penetration of said antigen through the epidermis or mucous membrane and Langerhans cell migration.

17. A topical method for enhancing an immune response against a tumor in a mammal comprising the steps of:
   providing a peptide antigen from said tumor which is about 3–20 amino acid residues in length,
   administering to an epidermal or mucous membrane site on said mammal a composition comprising the peptide antigen;
   administering to said epidermal or mucous membrane site a means for enhancing penetration of the peptide antigen through the epidermis or mucous membrane, said means for enhancing penetration being selected from the group consisting of a lipophilic solvent, low frequency ultrasound, electroporation iontophoresis and intraepidermal delivery; and
   administering to said epidermal or mucous membrane site a means for enhancing Langerhans cell migration.

18. The topical method of claim 17, wherein said means for enhancing penetration is low frequency ultrasound.

19. The topical method of claim 17, wherein said means for enhancing penetration is a lipophilic solvent selected from the group consisting of symmetrical or unsymmetrical alkylsulfide and alkylsulfoxides, wherein said alkyl group contains from 1 to 16 carbon atoms.

20. The topical method of claim 17, wherein said means for enhancing Langerhans cell migration is low frequency ultrasound.

21. The topical method of claim 17, wherein said means for enhancing Langerhans cell migration is selected from the group consisting of dibutylphthalate, dibutyl-D-tartarate, N,N-diethyl-toluamide, dibutylfumarate, di(2-ethylhexyl)fumarate, diisooctylmaleate, diethylhexylmaleate, diisooctylfumarate, benzoic acid, benzalkoniumchloride, bihenylmaleate, dioctylphthalate, dibutylmaleate, dioctymaleate, dibutylsuccinate, dioctylsuccinate, dinonylphthalate, diisononylphthalate, dimethylphthalate, diethylphthalate, dipropylphthalate, diphenylphthalate, dibenzylbutylphthalate, diethylmethylphthalate and camphor.

* * * * *

UNITED STATES PATENT AND TRADEMARK OFFICE
CERTIFICATE OF CORRECTION

PATENT NO. : 6,210,672 B1  
DATED : April 3, 2001  
INVENTOR(S) : Cowing

It is certified that error appears in the above-identified patent and that said Letters Patent is hereby corrected as shown below:

<u>Column 1,</u>  
Line 6, please add -- The government has certain rights in the invention. --

Signed and Sealed this

Eleventh Day of March, 2003

JAMES E. ROGAN  
*Director of the United States Patent and Trademark Office*